US012258267B2

(12) United States Patent
Becker et al.

(10) Patent No.: US 12,258,267 B2
(45) Date of Patent: Mar. 25, 2025

(54) APPARATUS AND METHOD FOR GENERATING OXYGEN FROM SODIUM PERCARBONATE AND WATER, INCLUDING SEAWATER

(71) Applicant: The United States of America, as represented by the Secretary of the Navy, San Diego, CA (US)

(72) Inventors: Carol A. Becker, Del Mar, CA (US); Wayne E. Glad, Del Mar, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 49 days.

(21) Appl. No.: 18/495,446

(22) Filed: Oct. 26, 2023

(65) Prior Publication Data
US 2024/0124304 A1   Apr. 18, 2024

Related U.S. Application Data

(62) Division of application No. 17/232,741, filed on Apr. 16, 2021, now Pat. No. 11,845,656.

(51) Int. Cl.
*C01B 13/02* (2006.01)
*A61M 16/10* (2006.01)
(Continued)

(52) U.S. Cl.
CPC ......... *C01B 13/0207* (2013.01); *A61M 16/10* (2013.01); *A62B 7/08* (2013.01);
(Continued)

(58) Field of Classification Search
CPC ............... C01B 13/0207; A61M 16/10; A61M 2202/0208; A62B 7/08; A62B 21/00; B01J 2208/00752
See application file for complete search history.

(56) References Cited

U.S. PATENT DOCUMENTS

| 4,508,700 A | 4/1985 | Hoshiko |
| 8,147,760 B1 | 4/2012 | Huvard |

(Continued)

FOREIGN PATENT DOCUMENTS

| CN | 1974002 B | * 7/2010 |
| JP | 4605680 B2 | * 1/2011 |
| WO | 2016/149030 | 9/2016 |

OTHER PUBLICATIONS

Catalytic Decomposition of Hydrogen Peroxide by Potassium Iodide. [online]. Rutgers School of Arts and Sciences [retrieved on Apr. 16, 2021]. Retrieved from the Internet: <URL: http://chem.rutgers.edu/cldf-demos/1019-cldf-demo-elephant-toothpaste>.

(Continued)

*Primary Examiner* — Imran Akram
(74) *Attorney, Agent, or Firm* — Naval Information Warfare Center Pacific; Kyle Eppele; Matthew D. Pangallo

(57) ABSTRACT

An apparatus and method generate oxygen gas from sodium percarbonate and water including seawater. The apparatus includes a chamber, a valve system, and an output port. The valve system controls combining a quantity of the sodium percarbonate, a quantity of the water, a quantity of potassium iodide, and optionally a quantity of sodium sulfate decahydrate. A chemical reaction between the sodium percarbonate and the water in the chamber generates oxygen gas, which is output at an output port from the chamber. The potassium iodide is a catalyst for the chemical reaction and optionally the sodium sulfate decahydrate is a temperature moderator for the chemical reaction. A ratio between the water and the sodium percarbonate is in a range of 2.5 to 8 by weight. A ratio of the potassium iodide per liter of the water yields a molarity in a range of 0.25 to 1.25.

10 Claims, 8 Drawing Sheets

(51) Int. Cl.
*A62B 7/08* (2006.01)
*A62B 21/00* (2006.01)

(52) U.S. Cl.
CPC ..... *A62B 21/00* (2013.01); *A61M 2202/0208* (2013.01); *B01J 2208/00752* (2013.01)

(56) References Cited

U.S. PATENT DOCUMENTS

| | | | |
|---|---|---|---|
| 10,556,135 | B2 | 2/2020 | Imbruce |
| 2002/0147123 | A1* | 10/2002 | Becker ................. C11D 17/06 510/530 |
| 2009/0038066 | A1* | 2/2009 | Kallmann ............. A47K 11/02 4/479 |
| 2010/0275362 | A1* | 11/2010 | Biesinger ............. A47K 11/02 4/483 |
| 2011/0203604 | A1* | 8/2011 | Hasegawa ............... A61Q 5/10 8/406 |

OTHER PUBLICATIONS

Nakano, Masayoshi, et al., "Exothermic Behavior of Thermal Decomposition of Sodium Percarbonate: Kinetic Deconvolution of Successive Endothermic and Exothermic Processes". J Phys. Chem. A 2015, 119, 9761-9769.

Becker-Glad, Carol, et al., "Acid Acceleration of Hydrogen Generation Using Seawater as a Reactant". International Journal of Hydrogen Energy 41 (Jul. 2016) 17761-17770.

Becker-Glad, Carol, et al., "A Chemical Oxygen Generator Using Seawater and a Chemical Oxygen Generator Using Seawater and Moderator to Control the Temperature". International Journal of Hydrogen Energy 45 (Sep. 2020) 29477-29491.

* cited by examiner

APPARATUS AND METHOD FOR GENERATING OXYGEN FROM SODIUM PERCARBONATE AND WATER, INCLUDING SEAWATER

REFERENCE TO RELATED APPLICATIONS

This application is a divisional of U.S. application Ser. No. 17/232,741 filed Apr. 16, 2021, now U.S. Pat. No. 11,845,656.

FEDERALLY-SPONSORED RESEARCH AND DEVELOPMENT

The United States Government has ownership rights in this invention. Licensing and technical inquiries may be directed to the Office of Research and Technical Applications, Naval Information Warfare Center Pacific, Code 72120, San Diego, CA, 92152; voice (619) 553-5118; ssc_pac_t2@navy.mil. Reference Navy Case Number 211848.

BACKGROUND OF THE INVENTION

In an oxygen-denied environment, such as subsea locations, oxygen can be obtained from pressurized gas cylinders. However, pressurized gas cylinders must be heavy to provide enough strength to withstand the pressure of a significant amount of oxygen. There is a general need for alternative sources of oxygen for oxygen-denied environments.

SUMMARY

An apparatus for generating oxygen gas from sodium percarbonate and water includes a chamber, a valve system, and an output port. The valve system controls combining a quantity of the sodium percarbonate, a quantity of the water, and a quantity of potassium iodide in the chamber. The output port from the chamber outputs the oxygen gas generated from a chemical reaction between the sodium percarbonate and the water in the chamber. The potassium iodide is a catalyst for the chemical reaction. A ratio between the water and the sodium percarbonate is in a range of 2.5 to 8 by weight. A ratio of the potassium iodide and the water yields a molarity in a range of 0.25 to 1.25 moles of the potassium iodide per liter of the water.

A method generates oxygen gas from sodium percarbonate and water. Combined in a chamber are a quantity of the sodium percarbonate, a quantity of the water, a quantity of potassium iodide, and optionally a quantity of sodium sulfate decahydrate. A ratio between the water and the sodium percarbonate is in a range of 2.5 to 8 by weight. A ratio of the potassium iodide and the water yields a molarity in a range of 0.25 to 1.25 moles of the potassium iodide per liter of the water. A chemical reaction between the sodium percarbonate and the water in the chamber generates oxygen gas, which is output at an output port from the chamber. The potassium iodide is a catalyst for the chemical reaction and optionally the sodium sulfate decahydrate is a temperature moderator for the chemical reaction. A ratio of the sodium sulfate decahydrate to the sodium percarbonate is in a range of zero to 75% of that needed to balance an endothermic heat of dissolution of an adduct of the sodium percarbonate and an endothermic heat of dissociation of the sodium sulfate decahydrate with an exothermic heat of formation of the oxygen gas.

BRIEF DESCRIPTION OF THE DRAWINGS

Throughout the several views, like elements are referenced using like references. The elements in the figures are not drawn to scale and some dimensions are exaggerated for clarity.

DETAILED DESCRIPTION OF EMBODIMENTS

The disclosed apparatus and method below may be described generally, as well as in terms of specific examples and/or specific embodiments. For instances where references are made to detailed examples and/or embodiments, it should be appreciated that any of the underlying principles described are not to be limited to a single embodiment, but may be expanded for use with any of the other methods and systems described herein as will be understood by one of ordinary skill in the art unless otherwise stated specifically.

Disclosed are alternative sources of oxygen for oxygen-denied environments, including subsea locations or terrestrial locations, such as within forest fires, where combustion of flammables has consumed all available atmospheric oxygen. The generated oxygen can be used for generating electricity from fuel cells or supporting human respiration. The alternative sources generate oxygen gas from a chemical reaction using various chemicals. For a subsea location, seawater forms the bulk of the mass of the required chemicals, with the remaining chemicals all being dry powders or dry granules, such that compact and unpressurized chemicals need transportation to the subsea location.

Figure 1:
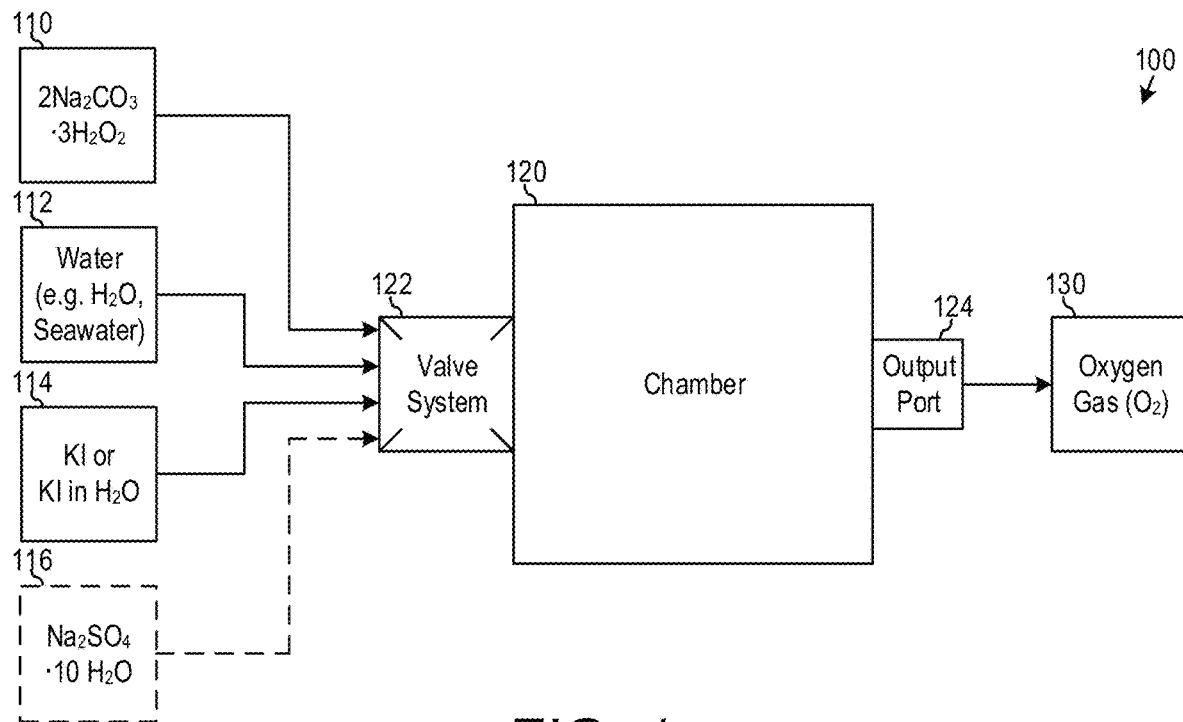
FIG. 1 is a schematic diagram of an apparatus for generating oxygen gas from sodium percarbonate and water in accordance with an embodiment of the invention.

FIG. 1 is a schematic diagram of an apparatus 100 for generating oxygen gas 130 from a quantity of sodium percarbonate ($2Na_2CO_3 \cdot 3H_2O_2$) 110 and a quantity of water 112 in accordance with an embodiment of the invention. The apparatus 100 includes a chamber 120, a valve system 122, and an output port 124. The water 112 is seawater, fresh water, deionized water, distilled water, or a mixture thereof.

The quantity of sodium percarbonate 110, the quantity of water 112, a quantity of potassium iodide (KI) 114, and an optional quantity of sodium sulfate decahydrate ($Na_2SO_4 \cdot 10H_2O$) 116 are combined in the chamber 120. The valve system 122 controls combining of the quantities of sodium percarbonate 110, water 112, potassium iodide 114, and the optional sodium sulfate decahydrate 116 in the chamber 120. An output port 124 from the chamber 120 outputs the oxygen gas 130 generated from a chemical reaction between the sodium percarbonate 110 and the water 112 in the chamber 120. The potassium iodide 114 is a catalyst for the chemical reaction.

A ratio between the water 112 and the sodium percarbonate 110 is in a range of 2.5 to 8 by weight. A ratio of the potassium iodide 114 and the water 112 yields a molarity in a range of 0.25 to 1.25 in chamber 120. In an embodiment with the potassium iodide 114 already dissolved in a solution in $H_2O$ before delivery through valve system 122 to chamber 120, this $H_2O$ is included with the water 112 for calculating the ratio in a range of 2.5 to 8 by weight between the water 112 and the sodium percarbonate 110, and this $H_2O$ is included with the water 112 for calculating the molarity in a range of 0.25 to 1.25 moles of the potassium iodide 114 per liter of the total water. In such an embodiment, the $H_2O$ delivered from the solution of the potassium iodide 114 is typically much less than that of the water 112.

While not being bound by theory, the Inventors believe the chemical reaction generates the oxygen gas 130 in a two-step process. The first step, Equation (1), is the dissociation of the adduct of the sodium percarbonate 110 in the water 112 in the chamber 120; the second step, Equations (2) and (3), is the decomposition of hydrogen peroxide to generate oxygen gas 130 with iodide (I⁻) from the potassium iodide 114 as a catalyst having an interim form hypoiodite (OI⁻).

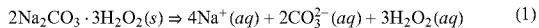

$$2Na_2CO_3 \cdot 3H_2O_2(s) \Rightarrow 4Na^+(aq) + 2CO_3^{2-}(aq) + 3H_2O_2(aq) \quad (1)$$

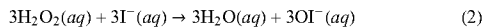

$$3H_2O_2(aq) + 3I^-(aq) \rightarrow 3H_2O(aq) + 3OI^-(aq) \quad (2)$$

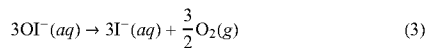

$$3OI^-(aq) \rightarrow 3I^-(aq) + \frac{3}{2}O_2(g) \quad (3)$$

In one embodiment, the optional sodium sulfate decahydrate 116 is included as a temperature moderator for the chemical reaction in the chamber 120. In another embodiment, the optional sodium sulfate decahydrate 116 is omitted, so that the apparatus 100 does not have a chemical that is a temperature moderator for the chemical reaction generating the hydrogen gas 130 in the chamber 120.

A chemical that is a temperature moderator is defined as a chemical that does not participate as a reactant or product in the chemical reaction generating the oxygen gas 130, including not participating in intermediate chemical reactions Equations (1), (2), and (3) above. A chemical that is a temperature moderator is defined as a chemical that significantly moderates temperature with a mechanism beyond the heat capacity of the chemical. For example, the chemical undergoes a phase transition that absorbs heat to moderate temperature. As so defined, $H_2O$ is not a chemical that is a temperature moderator for the chemical reaction that generates the oxygen gas 130 because $H_2O$ is a product, see Equation (2), and because $H_2O$ remains liquid during the chemical reaction, so that $H_2O$ only significantly moderates temperature through its heat capacity. Any humidity in the generated oxygen gas 130 insignificantly moderates temperature.

In contrast, the optional sodium sulfate decahydrate 116 is a temperature moderator as defined above. The sodium sulfate decahydrate 116 moderates temperature in several ways beyond its heat capacity. At 32° C., the sodium sulfate decahydrate 116 absorbs heat with a reversible phase transition from the decahydrate to an anhydrous form. During this phase transition, temperature is maintained at 32° C. The sodium sulfate decahydrate 116 has a different mechanism for moderating temperature below 32° C. The sodium sulfate decahydrate 116 has a relatively large endothermic heat of dissociation ($\Delta H$=79.4 kJ/mol). As the sodium sulfate decahydrate 116 dissolves into the water 112 in the chamber 120, the sodium sulfate decahydrate 116 takes in heat, suppressing any temperature increase in the chamber 120.

Although the sodium sulfate decahydrate 116 releases $Na^+(aq)$ ions upon dissolving into the water 112 in the chamber 120, and these $Na^+(aq)$ ions retard the reaction rate of Equation (1) above through the common ion effect, these $Na^+(aq)$ ions are product of dissolving the sodium sulfate decahydrate 116 into the water 112, and neither a reactant nor a product of the chemical reaction generating the oxygen gas 130.

In summary, because the sodium sulfate decahydrate 116 has mechanisms for moderating temperature beyond heat capacity, and because the sodium sulfate decahydrate 116 does not participate as a reactant or product in the chemical reaction generating the oxygen gas 130 in chamber 120, the sodium sulfate decahydrate 116 is a temperature moderator as defined above.

In an embodiment that includes the optional sodium sulfate decahydrate 116, the apparatus 100 includes a temperature moderator for the chemical reaction generating the oxygen gas 130 in the chamber 120, which temperature moderator is the sodium sulfate decahydrate 116. In an embodiment that omits the optional sodium sulfate decahydrate 116, the apparatus 100 does not have a chemical that is a temperature moderator for the chemical reaction generating the oxygen gas 130 in the chamber 120.

Figure 2:
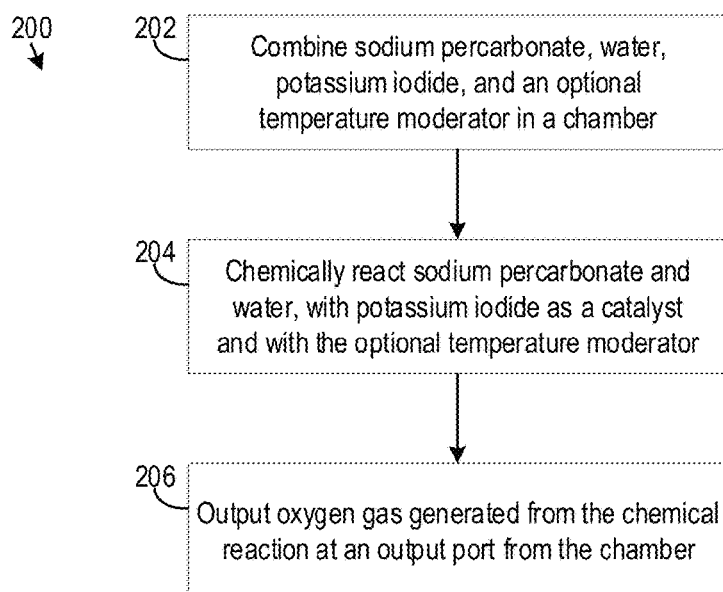
FIG. 2 is a flow diagram of a process for generating oxygen gas from sodium percarbonate and water in accordance with an embodiment of the invention.

FIG. 2 is a flow diagram of a process 200 for generating oxygen gas from sodium percarbonate and water in accordance with an embodiment of the invention.

At step 202, combined in a chamber are a quantity of the sodium percarbonate, a quantity of the water, a quantity of potassium iodide, and optionally a quantity of sodium sulfate decahydrate. A ratio between the water and the sodium percarbonate is in a range of 2.5 to 8 by weight. A ratio of the potassium iodide and the water yields a molarity in a range of 0.25 to 1.25 moles of the potassium iodide per liter of the water. The sodium percarbonate is an adduct, which is a loosely held combination of two molecules, sodium carbonate and hydrogen peroxide. A ratio between the sodium sulfate decahydrate and the sodium percarbonate is in a range of zero to 75% of that needed to balance an endothermic heat of dissolution of the adduct of the sodium percarbonate and an endothermic heat of dissociation of the sodium sulfate decahydrate with an exothermic heat of formation of the oxygen gas.

At step 204, the sodium percarbonate and the water chemically react in a chemical reaction in the chamber. The potassium iodide is a catalyst for the chemical reaction and optionally the sodium sulfate decahydrate is a temperature moderator for the chemical reaction. At step 206, the oxygen gas generated from the chemical reaction is output at an output port from the chamber.

Figure 3:
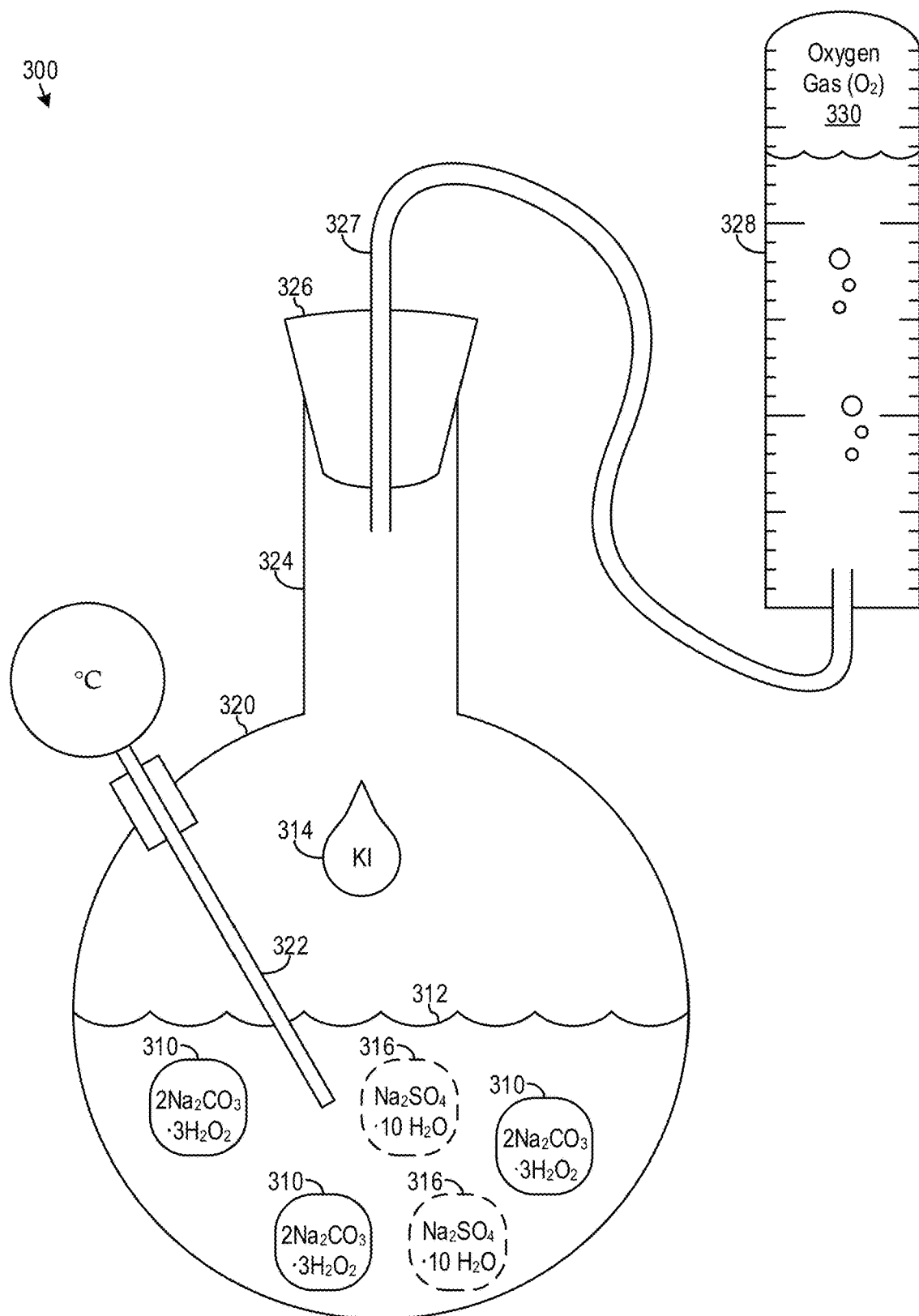
FIG. 3 is a schematic diagram of an experimental apparatus for generating oxygen gas from sodium percarbonate and water in accordance with embodiments of the invention.

FIG. 3 is a schematic diagram of an experimental apparatus 300 for generating oxygen gas 330 from sodium percarbonate 310 and water 312 in accordance with embodiments of the invention. The experimental apparatus 300 was used to produce the graphs 400, 410, 500, and 600 of FIG. 4, FIG. 5, and FIG. 6.

A flask 320 provides a chamber for combining chemicals for the chemical reaction that generates the oxygen gas 330. The flask 320 has a monitoring port, and a temperature probe 322 passes through the monitoring port for measuring a temperature during the chemical reaction. The temperature probe 322 measures a temperature of the reacting chemicals in the flask 320, and this measured temperature also is the temperature of the oxygen gas 330 generated from the chemical reaction in the flask 320.

The neck 324 of the flask 320 is an input/output port and the stopper 326 acts as a valve system controlling access to the flask 320 via neck 324. At the beginning of an experiment, the stopper 326 is removed and sodium percarbonate 310 and optionally sodium sulfate decahydrate 316 are introduced into the flask 320 via neck 324.

The sodium percarbonate 310 initially is in the form of dry granules with a coating impervious to atmospheric water vapor that would otherwise degrade the sodium percarbonate 310. For example, the sodium percarbonate 310 is commercially available as the granules of the laundry detergent additive "OxyClean." For consistency, 34.16 grams of the sodium percarbonate 310 were used in all experiments. This amount of sodium percarbonate 310 is the stoichiometric amount needed to produce four liters of oxygen gas 330 if the sodium percarbonate 310 was chemically pure. However, titration with standard permanganate showed that the sodium percarbonate 310 initially contained 86.1% of the stoichiometric hydrogen peroxide necessary to produce four liters of oxygen gas 330.

The optional sodium sulfate decahydrate 316 initially is in the form of a dry powder. When included, the powder of sodium sulfate decahydrate 316 was gently mixed with the granular sodium percarbonate 310, and the dry mixture was introduced into the flask 320 via neck 324.

Next, a measured amount of water 312 was introduced into the flask 320 via neck 324. The water 312 was seawater or deionized water depending upon the experiment. As soon as the water 312 mixes with the sodium percarbonate 310 in the flask 320, the sodium percarbonate 310 begins slowly decomposing and evolving oxygen gas; however, the reaction rate is so slow that the oxygen gas evolved before the addition of catalyst is negligible when the following steps are completed quickly.

A solution 314 of potassium iodide in $H_2O$ was added next via the neck 324 of the flask 320. The solution 314 had a high enough molarity so that a relatively small amount of the solution 314 was needed to achieve the target molarity of each experiment for moles of potassium iodide per liter of the total water including the water 312 and the $H_2O$ in the solution 314.

After adding the solution 314, the stopper 326 was immediately affixed to the neck 324 of the flask 320 because the potassium iodide is a catalyst that begins intense generation of the oxygen gas 330. The tubing 327 of the affixed stopper 326 is an output port, forcing the oxygen gas 330 into an inverted four-liter graduated cylinder 328. The inverted four-liter graduated cylinder 328 is initially filled with water, which is displaced with bubbling oxygen gas 330 generated from the chemical reaction in flask 320. The measurements of the generated amount of oxygen gas 330 are adjusted to compensate for the weight of the water in the graduated cylinder 328 reducing the pressure of the collected oxygen gas 330.

Figure 4:
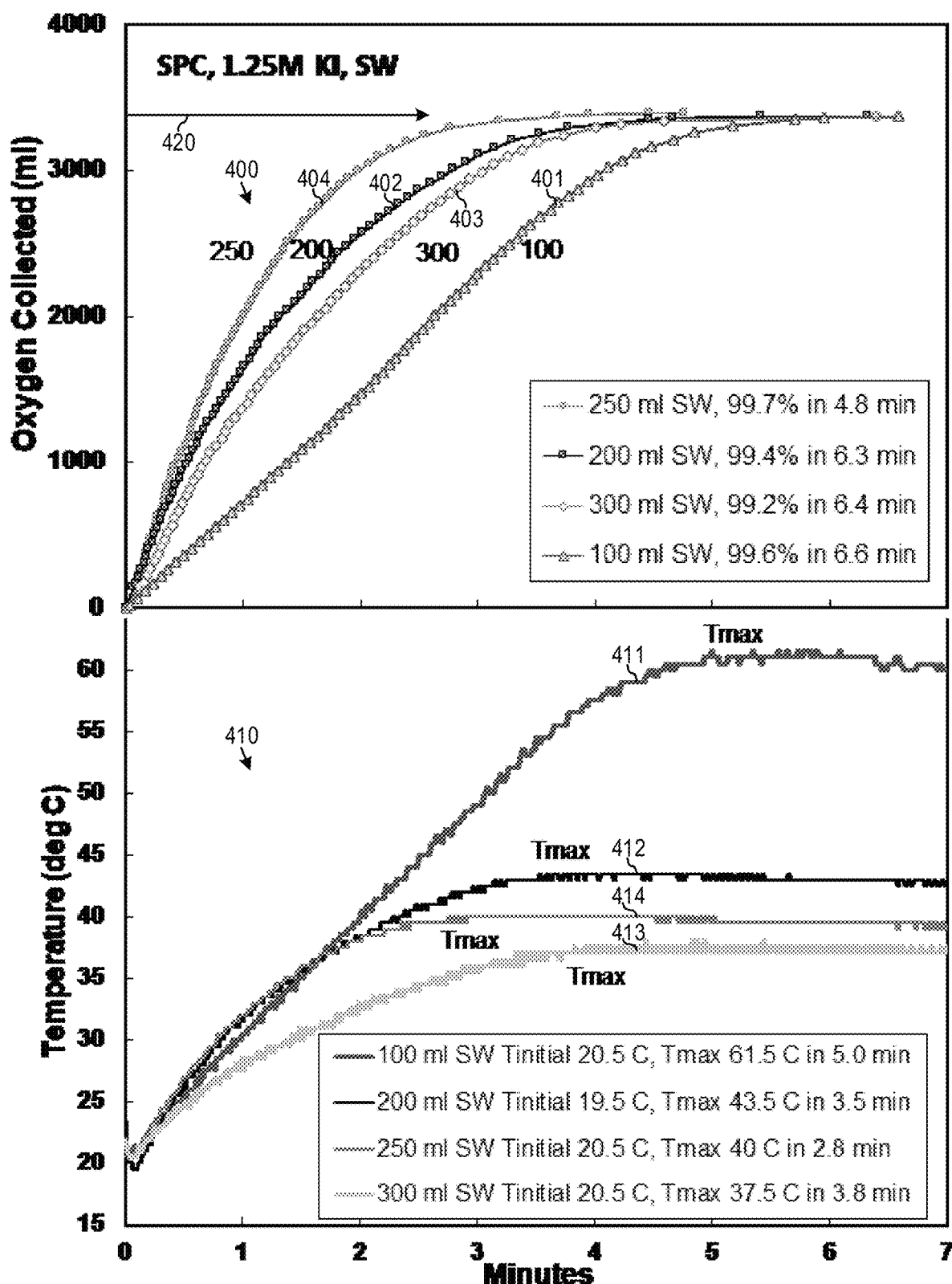
FIG. 4 is an oxygen collected graph and a temperature graph of generating oxygen gas from sodium percarbonate and seawater using the experimental apparatus of FIG. 3 in accordance with an embodiment of the invention.

FIG. 4 is an oxygen collected graph 400 and a temperature graph 410 of generating oxygen gas from sodium percarbonate and seawater using the experimental apparatus of FIG. 3 in accordance with an embodiment of the invention. The catalyst is potassium iodide at a molarity of 1.25 moles of per liter of total water. The initial focus of the experiments using the experimental apparatus of FIG. 3 was generating oxygen gas for a fuel cell operating in an undersea environment without any oxygen otherwise available. Accordingly, the first experiment was the 34.16 grams of the sodium percarbonate 310 in 100 ml of unfiltered seawater collected from the Pacific Ocean along the California coastline. Actual seawater was used because artificial seawater, which those skilled in the art have asserted is chemically equivalent to real seawater, was not actually equivalent and produced divergent results in other experiments.

Although water is not a temperature moderator as defined above, those of ordinary skill in the art understand that water has a significant heat capacity, which absorbs any heat released in the chemical reaction. For this reason, in the related art the amount of water is kept to a minimum so higher temperatures are reached during the chemical reaction and these higher temperatures promote a faster reaction.

Following this understanding in the related art, the initial experiment had the 34.16 grams of the sodium percarbonate in 100 ml (100 g) of the seawater, for a ratio of the seawater to the sodium percarbonate of 100/34.16=2.9 by weight. This baseline experiment produced a temperature curve 411 that reached a maximum temperature Tmax of 61.5° C., and produced an oxygen curve 401 that reached 99.6% of the expected yield 420 of oxygen gas in 6.6 minutes.

However, the Inventors noticed that much of the sodium percarbonate remained undissolved, resting unreactive on the bottom of the flask 320, until towards the end of the duration of the chemical reaction. The sodium percarbonate unexpectedly has dramatically less solubility in seawater than in deionized water. This is unexpected because the scientific literature appears to contain nothing regarding the decomposition of sodium percarbonate in seawater. A postulated explanation is the common ion effect, having Na ions from the salt in the seawater inhibit the dissolution of the sodium percarbonate. Furthermore, the catalyst of the related art is manganese dioxide ($MnO_2$), which is also dramatically impaired when instead using seawater, becoming an insoluble powder resting on top of the foam from the generated oxygen gas. In contrast, the non-transition metal catalyst potassium iodide is homogeneous, dissolving quickly and uniformly in water including seawater.

To establish an upper limit on the optimal ratio of seawater to sodium percarbonate, the next experiment tried increasing the amount of seawater. The next experiment increased the amount of seawater to 200 ml with the 34.16 grams of the sodium percarbonate, for a ratio of the seawater to the sodium percarbonate of 5.9. As expected, the resulting temperature curve 412 has of much lower maximum temperature Tmax of 43.5° C., primarily due to the doubled heat capacity after doubling the amount of seawater. However, completely unexpected was that despite the lower maximum temperature, the oxygen curve 402 shows faster oxygen gas generation than the oxygen curve 401, indicating the chemical reaction becomes much more energetic despite the lowered reaction temperature when the seawater is increased from 100 ml to 200 ml, especially at the beginning of the chemical reaction generating the oxygen gas.

To again attempt to establish an upper limit on the optimal ratio of seawater to sodium percarbonate, the next experiment increased the amount of seawater to 300 ml with the 34.16 grams of the sodium percarbonate, for a ratio of the seawater to the sodium percarbonate of 8.8. Again, the maximum temperature Tmax of 37.5° C. decreased for temperature curve 413. Oxygen curve 403 shows oxygen gas was generated somewhat slower than with 200 ml of the seawater, but oxygen gas was still generated much faster than with 100 ml of the seawater. Thus, 300 ml of the seawater establishes an upper limit on the optimal ratio of seawater to sodium percarbonate of 8.8 for maximizing the rate of generation of oxygen gas. However, a lower maximum temperature might be important for other optimization objectives.

The next experiment set the amount of seawater to 250 ml with the 34.16 grams of the sodium percarbonate, for a ratio of the seawater to the sodium percarbonate of 7.3. The temperature curve 414 has a maximum temperature Tmax of 40.0° C., and the oxygen curve 404 shows oxygen gas was generated faster than for the three other experiments, reaching 99.7% of the expected yield 420 of oxygen gas in 4.8 minutes. The Inventors were shocked with this discovery such a fast rate of generating oxygen gas at such a low maximum temperature achieved without a temperature moderator. While not being bound by theory, it appears the optimal ratio between the seawater and the sodium percarbonate is just enough seawater to fully dissolve the sodium percarbonate at the beginning of the chemical reaction generating the oxygen gas. The ratio of the seawater to the sodium percarbonate of 7.3 is approximately the optimal ratio for maximizing the rate of generating oxygen gas when the molarity of the potassium iodide is 1.25.

However, the ratio of 5.9 for oxygen curve 402 and the ratio of 8.8 for oxygen curve 403 have respective rates of generating oxygen gas higher than the rate for the ratio of 2.9 for oxygen curve 401 expected to be optimal in the related art, which teaches minimizing the amount of water. Thus, although the ratio of the seawater to the sodium percarbonate of 7.3 is approximately the optimal ratio for maximizing the rate of generating oxygen gas from sodium percarbonate and seawater, the entire range of 5.9 to 8.8 by weight, and especially the range of 7.0 to 8.0 by weight, between the seawater and the sodium percarbonate produces an unexpectedly fast rate of generating oxygen gas from sodium percarbonate and seawater without a temperature moderator.

Figure 5:
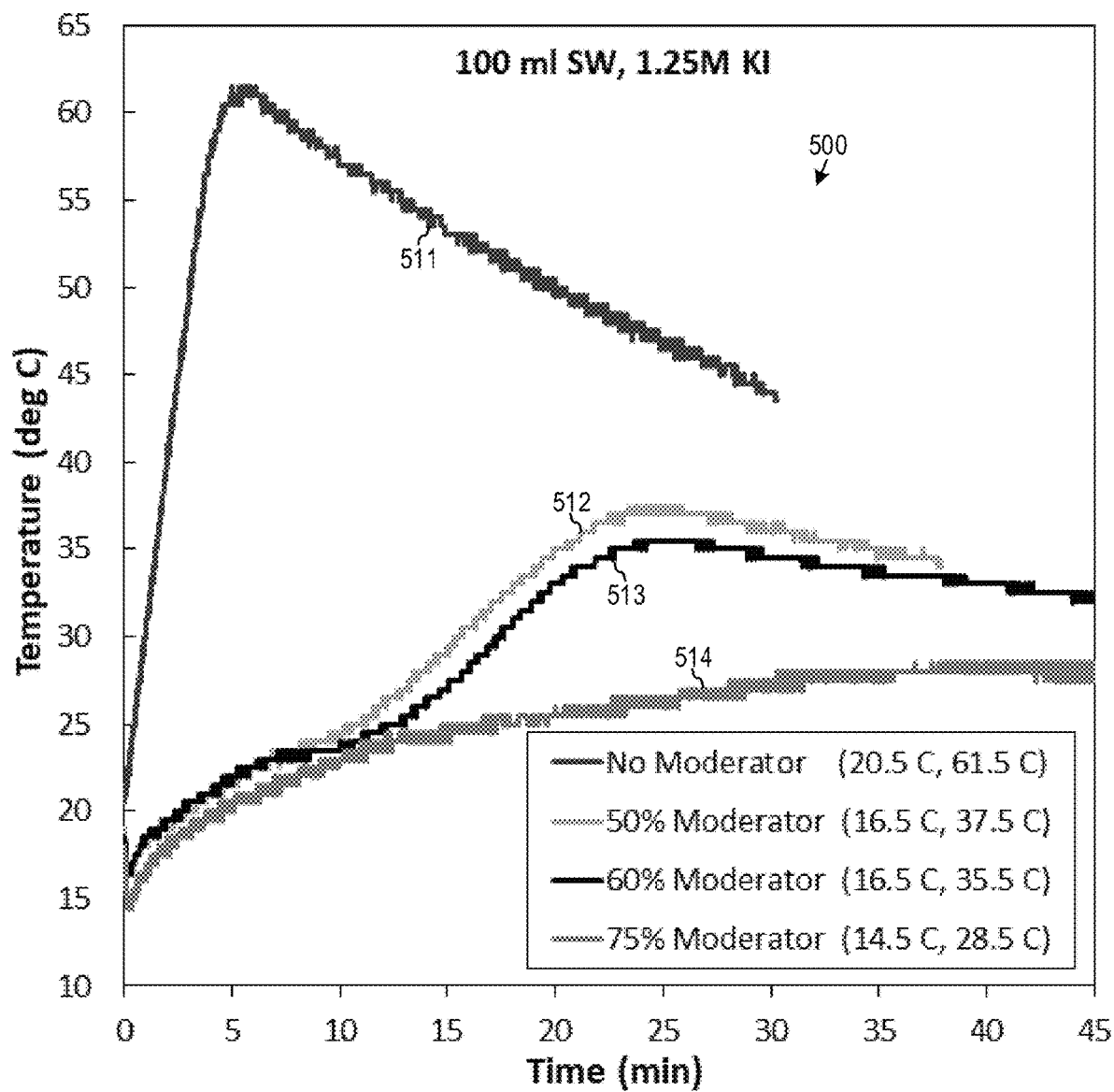
FIG. 5 is a temperature graph of generating oxygen gas from sodium percarbonate and seawater with a temperature moderator of sodium sulfate decahydrate using the experimental apparatus of FIG. 3 in accordance with an embodiment of the invention.

FIG. 5 is a temperature graph 500 of generating oxygen gas from sodium percarbonate and seawater with a temperature moderator of sodium sulfate decahydrate using the experimental apparatus of FIG. 3 in accordance with an embodiment of the invention. These experiments held the amount of seawater constant at 100 ml for a constant ratio of the seawater to the sodium percarbonate of 2.9, and held the potassium iodide constant at a molarity of 1.25 moles of per liter of total water, but measured the effect on reaction temperature from varying the amount of the temperature moderator of sodium sulfate decahydrate.

The baseline experiment with no moderator produced a temperature curve 511 that reached a maximum temperature Tmax of 61.5° C. This is the same baseline as a temperature curve 411 of FIG. 4, but FIG. 5 has a horizontal axis covering a longer duration of the chemical reaction. After reaching the maximum temperature Tmax of 61.5° C. when the chemical reaction completes, the temperature curve 511 decays upon releasing heat to the surroundings.

As discussed above, sodium sulfate decahydrate is a temperature moderator that takes in heat as it dissolves with a relatively large endothermic heat of dissociation ($\Delta H=79.4$ kJ/mol). The adduct of sodium percarbonate also takes in heat as it dissolves according to Equation (1) above. Thus, the dissolving sodium sulfate decahydrate and the dissolving sodium percarbonate both tend to lower temperature. The generation of oxygen gas according to Equations (2) and (3) above has an exothermic heat of formation that releases heat and tends to raise temperature. These counteracting tendencies to lower and raise temperature are balanced when an endothermic heat of dissolution of the adduct of the sodium percarbonate and an endothermic heat of dissociation of the sodium sulfate decahydrate equals an exothermic heat of formation of the oxygen gas. This balance is achieved at a particular ratio of the sodium sulfate decahydrate to the sodium percarbonate, determined to correspond to 107.18 grams of the sodium sulfate decahydrate for the 34.16 grams of the sodium percarbonate.

In addition to the baseline temperature curve 511 with no temperature moderator, temperature curves 512, 513, and 514 were measured for 50%, 60%, and 75% of the particular ratio between the sodium sulfate decahydrate and the sodium percarbonate that balances the endothermic heat of dissolution of the adduct of the sodium percarbonate and the endothermic heat of dissociation of the sodium sulfate decahydrate with the exothermic heat of formation of the oxygen gas.

Comparing FIG. 5 with FIG. 4, 50% of the heat balancing ratio between the sodium sulfate decahydrate and the sodium percarbonate achieves a maximum temperature of 37.5° C. for temperature curve 512 that equals the maximum temperature of 37.5° C. for temperature curve 412, but with only 100 ml of seawater instead of 300 ml of seawater, and with a longer duration for the reaction. Increasing the sodium sulfate decahydrate to 60% of the heat-balancing ratio further depresses the maximum temperature to 35.5° C. for temperature curve 513. Further increasing the sodium sulfate decahydrate to 75% of the heat-balancing ratio further depresses the maximum temperature to 28.5° C. for temperature curve 514, but the reaction duration increases to about an hour.

Therefore, when the optimization objective is to produce oxygen gas at a low temperature using a low amount of seawater while accepting a long duration for the reaction, this optimization objective is achieved when the ratio between the sodium sulfate decahydrate and the sodium percarbonate is 50%, 60%, or 75% of their heat-balancing ratio. A surprising result is that sodium sulfate decahydrate is such an effective temperature moderator achieving extremely low reaction temperatures. The related art uses different temperature moderators that do not achieve such extremely low reaction temperatures.

Figure 6:
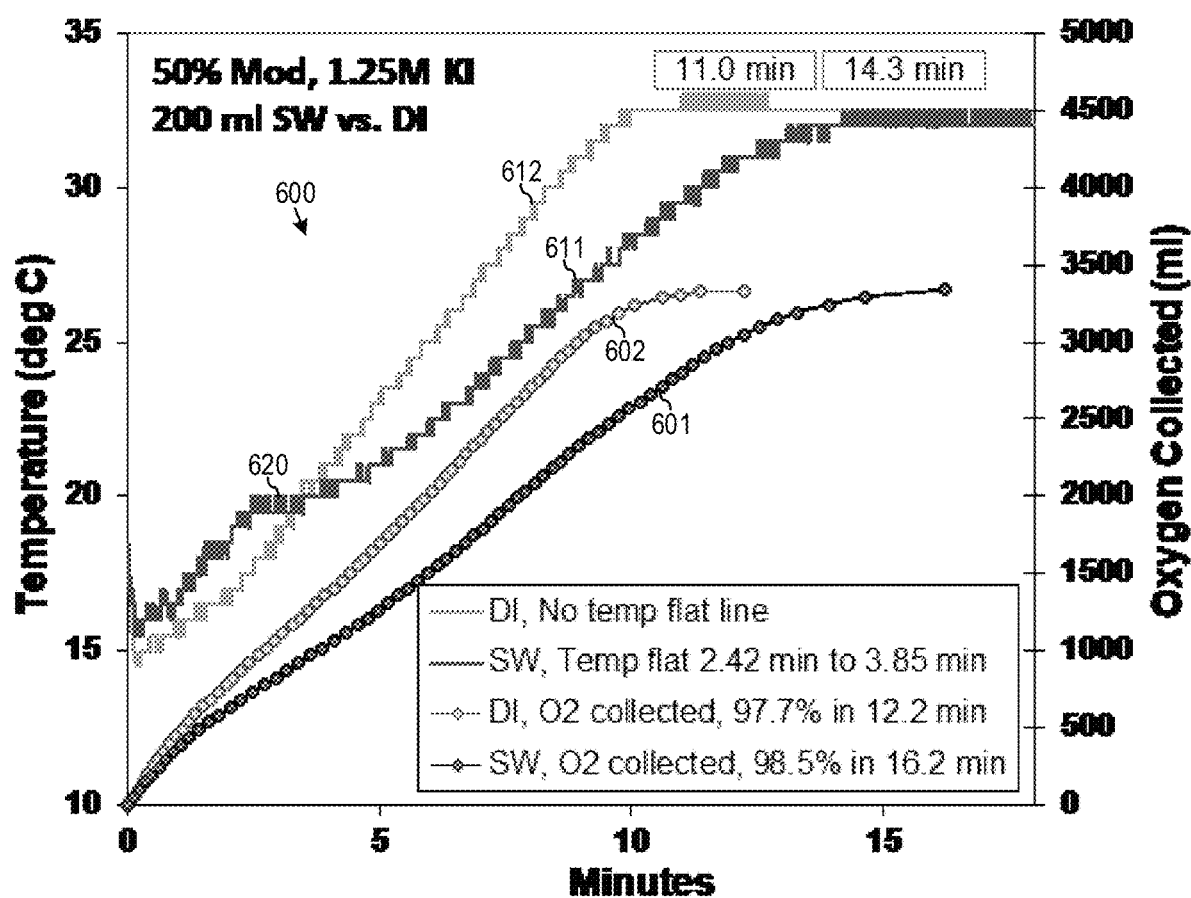
FIG. 6 is a graph of generating oxygen gas from sodium percarbonate and seawater or deionized water with a temperature moderator of sodium sulfate decahydrate using the experimental apparatus of FIG. 3 in accordance with an embodiment of the invention.

FIG. 6 is a graph 600 of generating oxygen gas from sodium percarbonate and seawater or deionized water with a temperature moderator of sodium sulfate decahydrate using the experimental apparatus of FIG. 3 in accordance with an embodiment of the invention. Two experiments share 34.16 grams of the sodium percarbonate, potassium iodide at a molarity of 1.25 moles of per liter of total water, and 50% of the heat-balancing ratio for the temperature moderator of sodium sulfate decahydrate, but one experiment uses 200 ml of seawater and the other use 200 ml of deionized water.

The temperature curve 611 for seawater has a portion that is a flat line 620, but the temperature curve 612 for deionized water does not have such a flat line. The temperature curve 612 and the oxygen curve 602 for deionized water show a higher rate for the chemical reaction than the temperature curve 611 and the oxygen curve 601 for seawater. This is primarily attributed to sodium percarbonate having higher solubility in deionized water than in seawater.

The flat line 620 of the temperature curve 611 for seawater is attributed to dissociation of the adduct of sodium percarbonate according to Equation (1) above. For seawater, the 50% moderator delays the peroxide decomposition step of Equations (2) and (3), so that the initial step of cracking the shells of the granular sodium percarbonate and dissociation of the adduct becomes visible. Because the sodium percarbonate is more soluble in deionized water, the dissolution and dissociation of the sodium percarbonate in deionized water occurs quickly despite the 50% moderator, so that the temperature curve 612 for deionized water does not have such a flat line. In summary, the flat line 620 of the temperature curve 611 for seawater supports that the chemical reaction generating the oxygen gas is a two-step process, with Equation (1) specifying the first step and Equations (2) and (3) specifying the second step.

Figure 7:
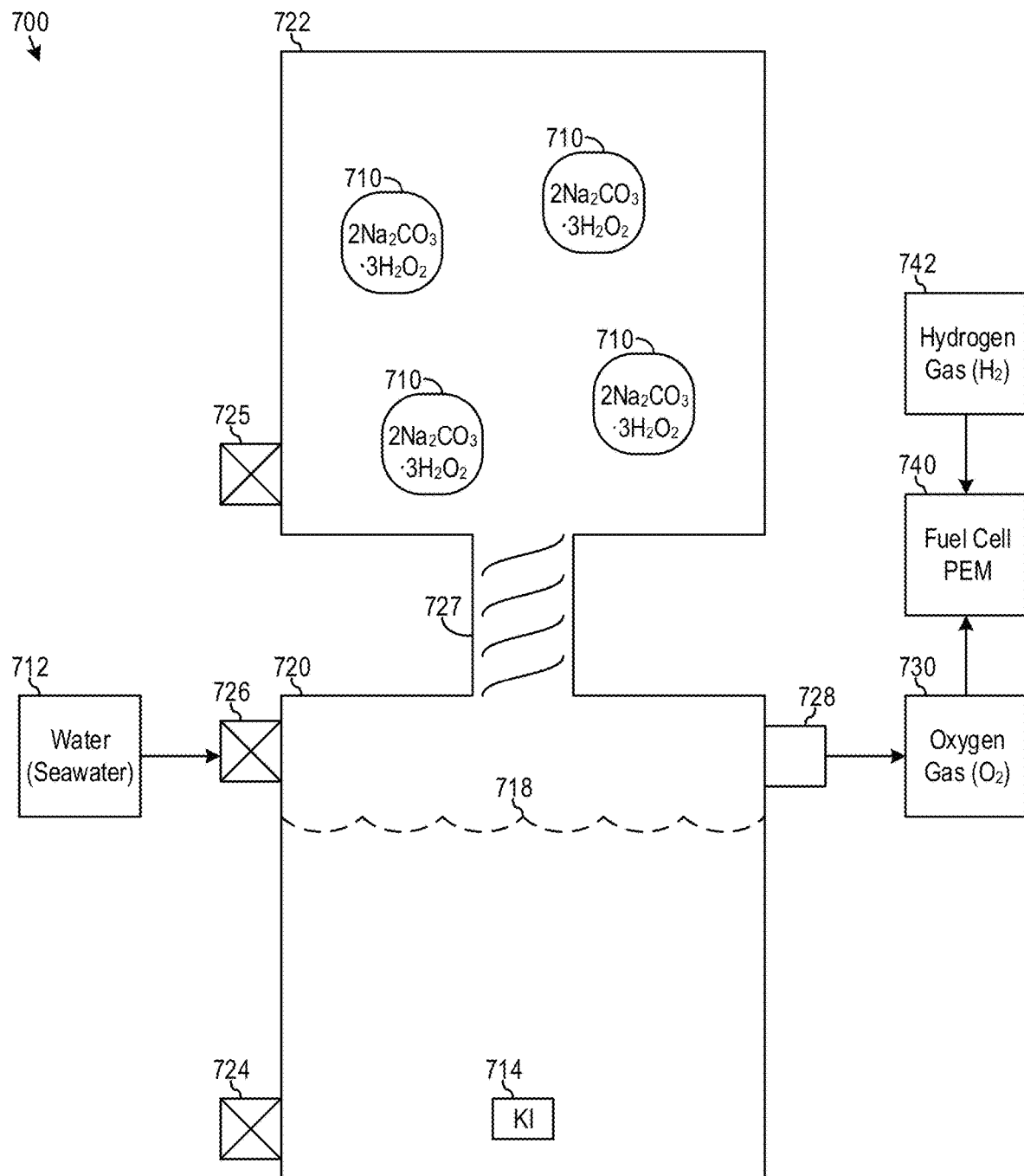
FIG. 7 is a schematic diagram of a fuel cell system that includes generating oxygen gas from sodium percarbonate and seawater in accordance with an embodiment of the invention.

FIG. 7 is a schematic diagram of a fuel cell system 700 that includes generating oxygen gas 730 from sodium percarbonate 710 and seawater 712 in accordance with an embodiment of the invention. This embodiment does not have a chemical that is a temperature moderator for the chemical reaction.

Initially, the chamber 720 stores in a dry state a quantity of the potassium iodide 714, and the chamber 722 stores in a dry state a quantity of coated granules of the sodium percarbonate 710. A valve system includes access ports 724 and 725. Initially, the quantity of the potassium iodide 714 is placed in the chamber 720 via access port 724, and the granules of the sodium percarbonate 710 are placed in the chamber 722 via access port 725.

Upon a demand for electricity from the fuel cell system 700, the valve 726 of the valve system admits a prescribed quantity of the seawater 712 into the chamber 720. The prescribed quantity of the seawater 712 is measured so that the ratio between the admitted seawater 712 and the sodium percarbonate 710 is in the range of 7.0 to 8.0 by weight. The seawater 712 quickly dissolves the potassium iodide 714 to form a solution 718 in chamber 720. The solution 718 has a molarity of in a range of 0.25 to 1.25 moles of the potassium iodide 714 per liter of the seawater 712.

The auger 727 of the valve system meters the granules of the sodium percarbonate 710 from the chamber 722 into the solution 718 in the chamber 720. Typically, the admitted seawater 712 fully dissolves the potassium iodide 714 before the auger 727 begins metering the granules of the sodium percarbonate 710. However, valve 726 and the auger 727 can be activated simultaneously.

The output port 728 outputs the oxygen gas 730 generated from the chemical reaction at a gas rate prescribed by a metering rate of the auger 727 of the valve system metering the granules of the sodium percarbonate 710 from the chamber 722 into the chamber 720. The fuel cell system 700 includes a fuel cell 740 supplied with the oxygen gas 730 generated from the chemical reaction in chamber 720. The fuel cell 740, such as a proton exchange membrane, generates electricity from hydrogen gas 742 and the oxygen gas 730. The metering rate of the auger 727 is prescribed to produce the oxygen gas 730 at a gas rate matching a demand for electricity from the fuel cell system 700.

The residue from the chemical reaction is the potassium iodide 714 and sodium carbonate ($Na_2CO_3$) dissolved in the solution 718. Because the seawater 712 includes some calcium and magnesium ions, a small amount of their insoluble carbonates might precipitate to form a cloudy solution 718 in the chamber 720. Access ports 724 and 725 permit cleaning the chemical residue from chambers 720 and 722, and then recharging the potassium iodide 714 and the sodium percarbonate 710.

Figure 8:
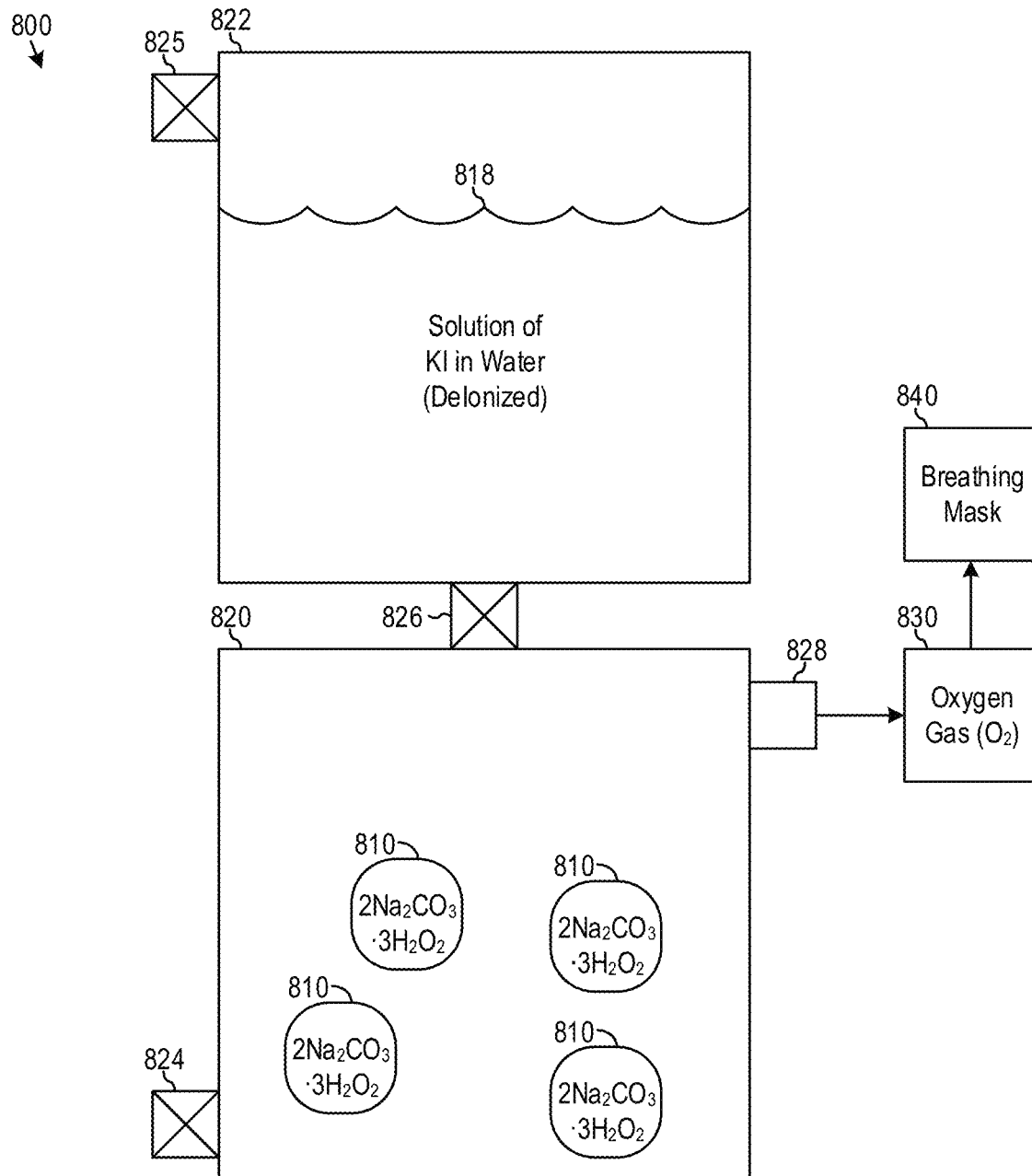
FIG. 8 is a schematic diagram of a breathing system for human respiration that generates oxygen gas from sodium percarbonate and deionized water in accordance with an embodiment of the invention.

FIG. 8 is a schematic diagram of a breathing system 800 for human respiration that generates oxygen gas 830 from sodium percarbonate 810 and deionized water or distilled water in accordance with an embodiment of the invention. This embodiment does not have a chemical that is a temperature moderator for the chemical reaction.

A valve system includes access ports 824 and 825. Initially, a quantity of coated granules of the sodium percarbonate 810 are placed in the chamber 820 via access port 824, and a solution 818, having a quantity of potassium iodide dissolved in a quantity deionized or distilled water, is placed in the chamber 822 via access port 825. The chamber 820 stores in a dry state the granules of the sodium percarbonate 810. The solution 818 has a molarity of in a range of 0.25 to 1.25 moles of the potassium iodide per liter of the deionized or distilled water.

The valve system includes also includes valve 826. Responsive to a demand requesting the oxygen gas 830, valve 826 dumps the solution 818 from chamber 822 into the chamber 820. During the subsequent chemical reaction, the introduced solution 818 dissolves the quantity of the sodium percarbonate 810 in the chamber 820, thereby combining of the sodium percarbonate 810, the potassium iodide, and the deionized or distilled water. The output port 828 outputs the oxygen gas 830 generated from the chemical reaction. A breathing mask 840 supplies the generated oxygen gas 830 for human respiration. The breathing mask 840 can include a bag that inflates to store any excess oxygen gas 830 not immediately needed for human respiration.

A ratio between the water in the solution 818 and the sodium percarbonate 810 is in a range of 5.0 to 6.5 by weight. Experiments using the experimental apparatus of FIG. 3 show the unexpected result that this ratio produces a maximum temperature of 44° C. for the chemical reaction without any temperature moderator. In one example, an experiment with 34.16 grams of the sodium percarbonate and potassium iodide at a molarity of 1.25 moles of per liter in 200 ml of the deionized or distilled water, but no temperature moderator, has a ratio between the water in the solution 818 and the sodium percarbonate 810 of 5.9 by weight. This experiment produced 99.4% of the stoichiometric amount of oxygen gas 830 in 5.8 minutes with a maximum temperature for the chemical reaction in the chamber 820 of 44° C.

Because the breathing system 800 generates nearly four liters of oxygen gas 830 during the chemical reaction over 5.8 minutes, and because the breathing system 800 generates the oxygen gas 830 at a temperature less than or equal to the maximum temperature of 44° C., the breathing system 800 generates the oxygen gas 830 at a rate and safe temperature sustaining human respiration. This is accomplished without any temperature moderator. The result that the breathing system 800 generates the oxygen gas 830 at a rate and the temperature sustaining human respiration without any temperature moderator is an unexpected result over the related art, which teaches a temperature moderator is required to generate oxygen gas from a chemical reaction at a temperature low enough to sustain human respiration.

Figure 9:
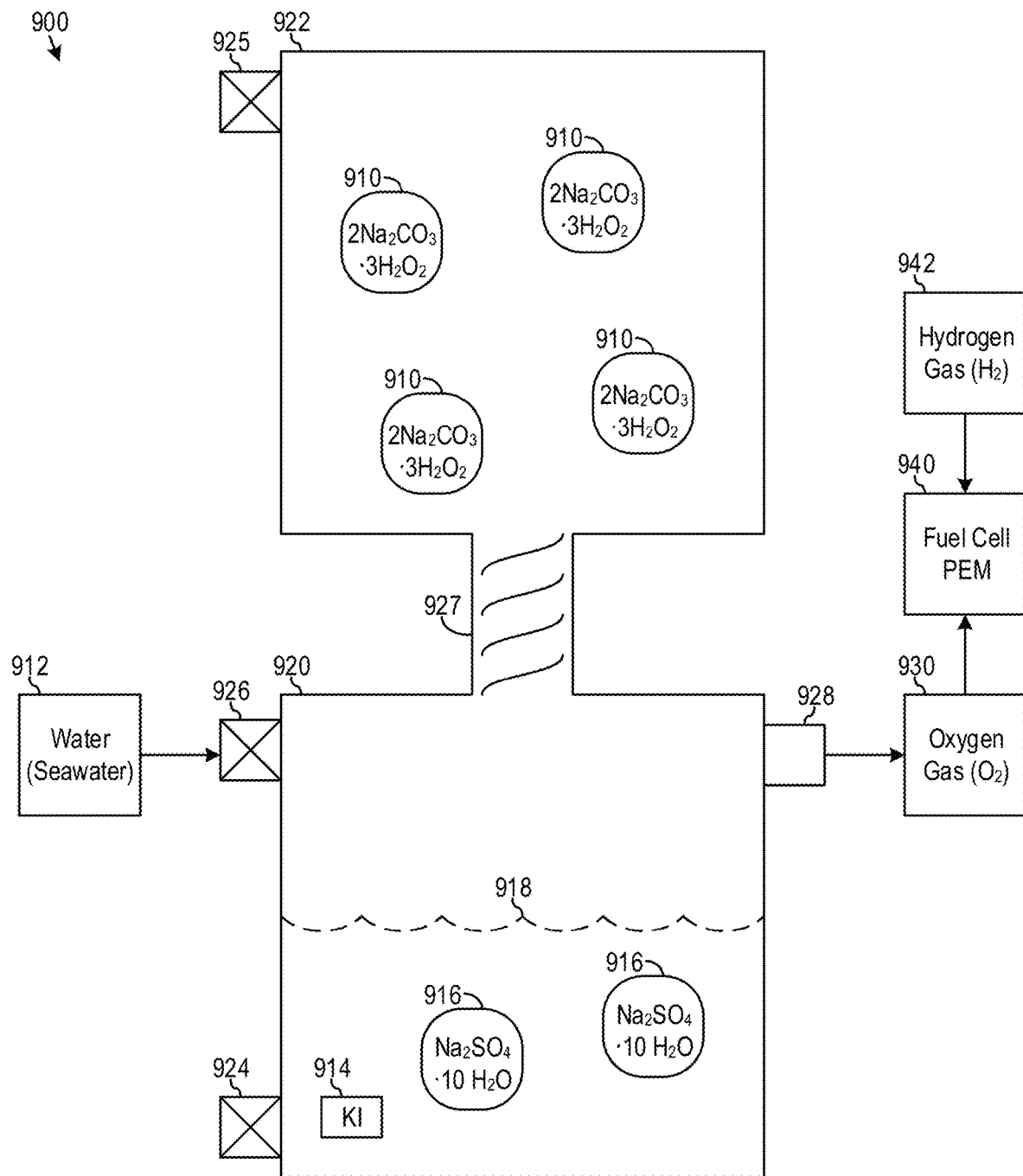
FIG. 9 is a schematic diagram of a fuel cell system that generates oxygen gas from sodium percarbonate and seawater using a temperature moderator in accordance with an embodiment of the invention.

FIG. 9 is a schematic diagram of a fuel cell system 900 that generates oxygen gas 930 from sodium percarbonate 910 and seawater 912 using a temperature moderator in accordance with an embodiment of the invention. This embodiment includes sodium sulfate decahydrate 916 as the temperature moderator for the chemical reaction generating oxygen gas 930. The result that sodium sulfate decahydrate 916 achieves extremely low reaction temperatures is a surprising result over the related art, which teaches using different temperature moderators that do not achieve such extremely low reaction temperatures.

Initially, the chamber 920 stores in a dry state a quantity of potassium iodide 914 and a non-zero quantity of the sodium sulfate decahydrate 916, and the chamber 922 stores in a dry state coated granules of the sodium percarbonate 910. Responsive to a demand requesting the oxygen gas 930, valve 926 of a valve system admits a prescribed quantity of the seawater 912 into the chamber 920 to form a solution 918 of the potassium iodide 914, the sodium sulfate decahydrate 916, and the prescribed quantity of the seawater 912. Responsive further to the demand requesting the oxygen gas 930 for the fuel cell 940, auger 927 of the valve system meters the sodium percarbonate 910 from the chamber 922 into the solution 918 in the chamber 920.

Thus, to generate the oxygen gas 930, combined in chamber 920 are the quantity of the sodium percarbonate 910, the prescribed quantity of the seawater 912, the quantity of the potassium iodide 914, and the quantity of the sodium sulfate decahydrate 916. A ratio between the seawater 912 and the sodium percarbonate 910 is in a range of 2.5 to 3.5 by weight. The solution 918 has a molarity of in a range of 0.25 to 1.25 moles of the potassium iodide 914 per liter of the seawater 912. A ratio between the sodium sulfate decahydrate 916 and the sodium percarbonate 910 is in a range of 50% to 75% of that needed to balance an endothermic heat of dissolution of the adduct of the sodium percarbonate 910 and an endothermic heat of dissociation of the sodium sulfate decahydrate 916 with an exothermic heat of formation of the oxygen gas 930.

The output port 928 outputs the oxygen gas 930 generated in the chamber 920 from the chemical reaction at a gas rate prescribed by a metering rate of auger 927 metering the sodium percarbonate 910 from the chamber 922 into the chamber 920. Upon a demand for generating electricity from the fuel cell system 900, hydrogen gas 942 and the generated oxygen gas 930 are supplied to a fuel cell 940, which generates the electricity.

The residue from the chemical reaction is the potassium iodide 914, sodium sulfate ($Na_2SO_4$) from the sodium sulfate decahydrate 916, and the sodium carbonate ($Na_2CO_3$) from the sodium percarbonate 910, all dissolved in the solution 918. Access ports 924 and 925 permit cleaning the chemical residue from chambers 920 and 922, and then recharging the potassium iodide 914, the sodium sulfate decahydrate 916, and the sodium percarbonate 910.

From the above description of the Apparatus and Method for Generating Oxygen from Sodium Percarbonate and Water, Including Seawater, it is manifest that various techniques may be used for implementing the concepts of process 200 and apparatus 100, 300, 700, 800, or 900 without departing from the scope of the claims. The described embodiments are to be considered in all respects as illustrative and not restrictive. The system/method disclosed herein may be practiced in the absence of any element that is not specifically claimed and/or disclosed herein. It should also be understood that process 200 or apparatus 100, 300, 700, 800, or 900 is not limited to the particular embodiments described herein, but is capable of many embodiments without departing from the scope of the claims.

We claim:

1. A method for generating oxygen gas from sodium percarbonate and water comprising:
   combining a first quantity of the sodium percarbonate, a second quantity of the water, a third quantity of potassium iodide, and a fourth quantity of sodium sulfate decahydrate in a chamber, wherein:
     a first ratio of the second quantity to the first quantity is in a first range of 2.5 to 8 by weight between the water and the sodium percarbonate,
     a second ratio of the third quantity to the second quantity yields a molarity in a second range of 0.25 to 1.25 moles of the potassium iodide per liter of the water, and
     a third ratio of the fourth quantity to the first quantity is in a third range of greater than zero to 75% of that needed to balance an endothermic heat of dissolution of an adduct of the sodium percarbonate and an endothermic heat of dissociation of the sodium sulfate decahydrate with an exothermic heat of formation of the oxygen gas;
   chemically reacting a chemical reaction between the sodium percarbonate and the water in the chamber, wherein the potassium iodide is a catalyst for the chemical reaction and the sodium sulfate decahydrate is a temperature moderator for the chemical reaction; and
   outputting the oxygen gas generated from the chemical reaction at an output port from the chamber.

2. The method of claim 1, wherein the water is selected from the group consisting of seawater, fresh water, deionized water, distilled water, and a mixture thereof.

3. The method of claim 1, wherein:
   the water is seawater, and
   the first ratio of the second quantity to the first quantity is in the first range of 7.0 to 8.0 by weight between the seawater and the sodium percarbonate; and
   the outputting of the oxygen gas includes outputting the oxygen gas to a fuel cell.

4. The method of claim 1, wherein:
   the water is deionized water or distilled water, and
   the first ratio of the second quantity to the first quantity is in the first range of 5.0 to 6.5 by weight between the water and the sodium percarbonate; and
   the outputting of the oxygen gas includes outputting the oxygen gas at a rate and a temperature less than or equal to a maximum temperature of 44° C. for sustaining human respiration.

5. The method of claim 1, wherein the third ratio of the fourth quantity to the first quantity is in the third range of 50% to 75% of that needed to balance an endothermic heat of dissolution of an adduct of the sodium percarbonate and an endothermic heat of dissociation of the sodium sulfate decahydrate with an exothermic heat of formation of the oxygen gas.

6. The method of claim 1, wherein the combining includes:
   storing the first quantity of the sodium percarbonate and the fourth quantity of the sodium sulfate decahydrate in the chamber in a dry state; and
   responsive to a demand requesting the oxygen gas, introducing into the chamber a solution of the third quantity of the potassium iodide in the second quantity of the water.

7. The method of claim 6, wherein the introducing of the solution includes:
dissolving the third quantity of the potassium iodide in the second quantity of the water to form the solution; and
combining the solution with the first quantity of the sodium percarbonate and the fourth quantity of the sodium sulfate decahydrate in the chamber.

8. The method of claim 1, wherein
the combining includes:
storing a mixture of the third quantity of the potassium iodide and a non-zero amount of the fourth quantity of the sodium sulfate decahydrate in a dry state in the chamber that is a first chamber;
storing the first quantity of the sodium percarbonate in a dry state in a second chamber;
responsive to a demand requesting the oxygen gas, admitting the second quantity of the water into the first chamber to form a solution of the third quantity of the potassium iodide, the fourth quantity of the sodium sulfate decahydrate, and the second quantity of the water in the first chamber; and
responsive further to the demand requesting the oxygen gas, metering the sodium percarbonate from the second chamber into the solution in the first chamber; and
the outputting the oxygen gas includes:
outputting the oxygen gas generated in the first chamber from the chemical reaction at a gas rate prescribed by a metering rate of the metering of the sodium percarbonate from the second chamber to the first chamber.

9. A method for generating oxygen gas from sodium percarbonate and seawater, the method comprising
combining a first quantity of the sodium percarbonate, a second quantity of the seawater, and a third quantity of potassium iodide in a chamber, wherein:
a first ratio of the second quantity to the first quantity is in a first range of 2.5 to 8 by weight between the seawater and the sodium percarbonate, and
a second ratio of the third quantity to the second quantity yields a molarity in a second range of 0.25 to 1.25 moles of the potassium iodide per liter of the seawater;
chemically reacting a chemical reaction between the sodium percarbonate and the seawater in the chamber, wherein the potassium iodide is a catalyst for the chemical reaction; and
outputting the oxygen gas generated from the chemical reaction at an output port from the chamber.

10. The method of claim 9, wherein:
the first ratio of the second quantity to the first quantity is in the first range of 7.0 to 8.0 by weight between the seawater and the sodium percarbonate; and
the outputting of the oxygen gas includes outputting the oxygen gas to a fuel cell.

* * * * *